(12) United States Patent  
Hansen et al.

(10) Patent No.: US 6,222,092 B1  
(45) Date of Patent: *Apr. 24, 2001

(54) ABSORBENT GARMENT WITH TOP SHEET IMPEDIMENT TO LIQUID FLOW

(75) Inventors: Ebba A. Hansen; Andrew Baker, both of Lawrenceville, GA (US)

(73) Assignee: Paragon Trade Brands, Inc., Norcross, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/897,621

(22) Filed: Jul. 21, 1997

Related U.S. Application Data

(63) Continuation of application No. 08/519,802, filed on Aug. 28, 1995, now abandoned.

(51) Int. Cl.[7] ..................................................... A61F 13/15
(52) U.S. Cl. ................. 604/378; 604/385.01; 604/385.1; 604/385.23; 428/138
(58) Field of Search ........................... 604/348, 350–351, 604/355, 358, 365–370, 372, 374–376, 378–384, 389–397, 399; 428/131, 134–138, 170–172, 284, 913

(56) References Cited

U.S. PATENT DOCUMENTS

| | | | |
|---|---|---|---|
| 2,877,765 | * | 3/1959 | Bunyan .................................. 604/358 |
| 3,367,333 | * | 2/1968 | Scheier .................................. 604/384 |
| 3,559,648 | | 2/1971 | Mason, Jr. . |
| 3,572,342 | | 3/1971 | Lindquist et al. . |

(List continued on next page.)

FOREIGN PATENT DOCUMENTS

| | | |
|---|---|---|
| 0376022 A3 | 12/1988 | (EP) . |
| 0523719 A1 | 7/1991 | (EP) . |
| WO 93/12749 | 7/1993 | (WO) . |

OTHER PUBLICATIONS

Webster's II New Riverside University Dictionary, pp. 1095 and 340, Copyright 1984,1988,1994.*
Webster's II New Riverside University Dictionary, pp. 340, 384, 1095, Copyright 1984, 1988, 1994 by Houghton Mifflin Company.*
EP 273454–B1, Uni Charm Corp. (abstract).
WO 9312749–A1, Procter & Gamble Co. (abstract).
U.S. Patent No. 5,158,821, Hoechst AG (abstract).

Primary Examiner—Dennis Ruhl
(74) Attorney, Agent, or Firm—Hunton & Williams

(57) ABSTRACT

A disposable absorbent garment has barrier elements on its inner liner to form barriers to flow of urine across the liner surface. In one embodiment, the barrier elements are loops formed by rows of slits through the liner material, such that the slits form rows of strips. Central portions of the strips are forced out of the plane of the liner to form wide based loops or humps on the inner surface of the garment when the garment is in place about the body of a wearer. These elevated loops form rows of raised obstructions that act as urine flow interference barriers. In other embodiments, the loops are preformed on the surface of the liner layer, or are formed from interdigitating strips. The loops are preferably provided in a target area of the garment where urine impinges the liner surface. Garments intended to be worn by males may have the loops distributed primarily throughout a front crotch region, to interfere with the substantially tangential movement of urine across the liner layer. The garment diminishes leakage of urine out of the waistband of the garment, and inhibits migration of liquid waste within the diaper. Apertures formed under the loops provide an opening through which liquid waste enters the interior of the garment.

27 Claims, 6 Drawing Sheets

U.S. PATENT DOCUMENTS

| | | | | |
|---|---|---|---|---|
| 3,665,921 | * | 5/1972 | Stumpf | 604/366 |
| 3,766,922 | | 10/1973 | Krusko . | |
| 3,814,101 | * | 6/1974 | Kozak | 604/378 |
| 3,886,941 | | 6/1975 | Duane et al. . | |
| 3,967,623 | * | 7/1976 | Butterworth et al. | 604/383 |
| 4,036,233 | * | 7/1977 | Kozak | 604/383 |
| 4,050,462 | | 9/1977 | Woon et al. . | |
| 4,077,410 | * | 3/1978 | Butterworth et al. | 604/366 |
| 4,300,562 | | 11/1981 | Pieniak . | |
| 4,323,069 | | 4/1982 | Ahr et al. . | |
| 4,389,211 | * | 6/1983 | Lenaghan | 604/383 |
| 4,443,512 | | 4/1984 | Delvaux . | |
| 4,460,642 | | 7/1984 | Errede et al. . | |
| 4,460,648 | | 7/1984 | Kondo et al. . | |
| 4,535,020 | * | 8/1985 | Thomas et al. | 604/383 |
| 4,547,420 | | 10/1985 | Krueger et al. . | |
| 4,560,372 | | 12/1985 | Pleniak . | |
| 4,643,727 | | 2/1987 | Rosenbaum . | |
| 4,704,112 | | 11/1987 | Suzuki et al. . | |
| 4,741,941 | | 5/1988 | Englebert et al. . | |
| 4,772,444 | | 9/1988 | Curro et al. . | |
| 4,773,905 | | 9/1988 | Molee et al. . | |
| 4,778,459 | | 10/1988 | Fuisz . | |
| 4,842,596 | | 6/1989 | Kielpikowski et al. . | |
| 4,891,258 | * | 1/1990 | Fahrenkrug | 604/358 |
| 4,895,568 | | 1/1990 | Enloe . | |
| 4,908,026 | | 3/1990 | Sukiennik et al. . | |
| 4,968,312 | | 11/1990 | Khan . | |
| 4,990,147 | | 2/1991 | Freeland . | |
| 5,023,124 | * | 6/1991 | Kobayashi | 428/76 |
| 5,092,861 | | 3/1992 | Nomura et al. . | |
| 5,151,091 | | 9/1992 | Glaug et al. . | |
| 5,158,819 | | 10/1992 | Goodman, Jr. et al. . | |
| 5,188,625 | | 2/1993 | Van Iten et al. . | |
| 5,236,428 | | 8/1993 | Zajacakowski . | |
| 5,254,111 | | 10/1993 | Cancio et al. . | |
| 5,268,213 | | 12/1993 | Murakami et al. . | |
| 5,308,344 | | 5/1994 | Toth . | |
| 5,318,553 | | 6/1994 | Weeks et al. . | |
| 5,368,910 | * | 11/1994 | Langdon | 604/358 |
| 5,536,555 | * | 7/1996 | Zelazoski et al. | 604/358 |

* cited by examiner

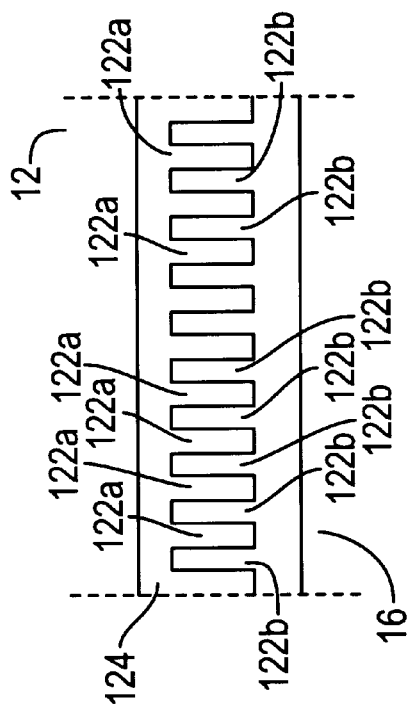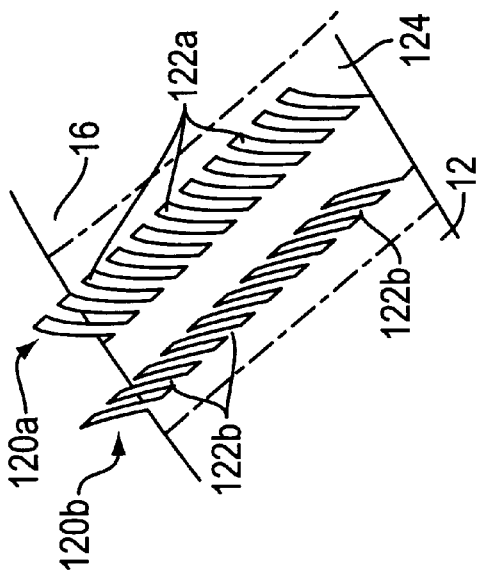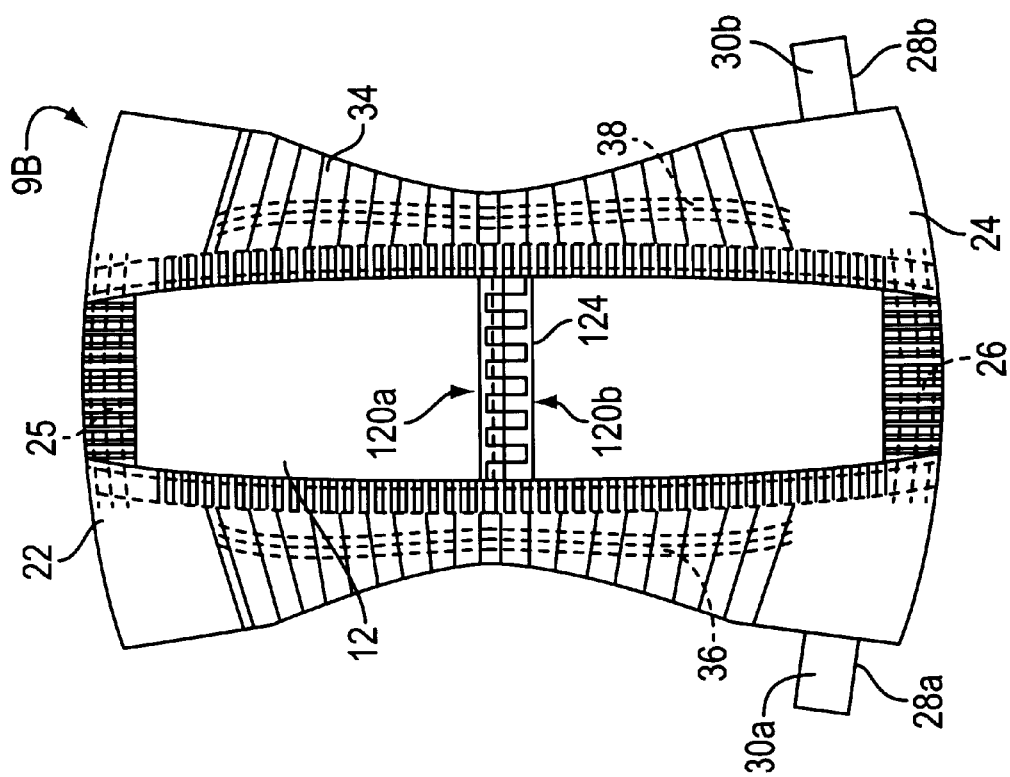

ABSORBENT GARMENT WITH TOP SHEET IMPEDIMENT TO LIQUID FLOW

This application is a continuation of application Ser. No. 08/519,802, filed Aug. 28, 1995, now abandoned.

FIELD OF THE INVENTION

This invention relates to an absorbent garment, and more particularly such a garment that has impediments on its surface to inhibit flow of liquid across the surface to edges of the garment.

BACKGROUND OF THE INVENTION

Disposable absorbent garments are well known in the art. Such garments typically include a moisture-impervious backing sheet, an absorbent pad, and a liner sheet that contacts the body of a person wearing the garment. In addition, elasticized regions are provided around the edges of the garment for securing it about the waist and legs of a wearer. Disposable diapers having elasticized margins for placement about the legs of a wearer are disclosed in U.S. Pat. No. 4,050,462 and U.S. Pat. No. 5,092,861. An absorbent article having elasticized side margins and waistband margins is shown in U.S. Pat. No. 4,300,562.

Despite previous advancements in the field of absorbent garments, persons skilled in the art continue their efforts to produce more comfortable garments which are better able to contain urinary and fecal excretions. For instance, problems with prior diaper designs include leakage of urinary or fecal material from the garment. Prolonged contact of liquid or semi-solid excreta with the skin of the wearer is also a continuing problem in the art. Recent absorbent garments have utilized passageways through the liner sheet to help contain such excretions, and more rapidly remove them from contact with the wearer. For instance, U.S. Pat. No. 4,990,147 and U.S. Pat. No. 4,968,312 describe absorbent articles having a passageway through the liner that helps convey waste from the skin of the wearer.

Yet another approach to the problem of diapers leaking excreta is to provide on the diaper lining an elevated barrier to direct movement of waste within the diaper during use. For example, U.S. Pat. No. 3,572,342 describes a flexible, resilient hydrophobic strip that may be placed between the area of the diaper into which excretion occurs, and the waist bands or leg gathers. U.S. Pat. No. 5,268,213 discloses longitudinally extending ribs with convex top surfaces that guide body fluids in a longitudinal direction along the interior surface of the diaper. This ribbed design is said to distribute the fluid evenly across the interior surface of the diaper.

U.S. Pat. No. 4,895,568 discloses a disposable diaper having a resilient barrier member that extends from the inner liner toward the body of the wearer and inhibits the longitudinal movement of liquid or viscous waste material between the front and rear sections of the diaper. In one embodiment, the barrier is a continuous linear polymer foam ridge member that extends transversely across the inner liner of the diaper. In an alternative embodiment, the barrier is provided by a plurality of parallel, longitudinally extending elastic members that form ruffles aligned in a transverse row across the liner layer. The barriers are said to provide an isolation pocket at the rear section of the diaper, or at a fluid insult target zone in the front section of the diaper. The ruffles are further described as helping reduce wrinkles in the liner layer so that liquid penetrates more rapidly through the liner.

Another problem with disposable diaper garments is that the relationship of the garment to the anatomy of the user varies depending on the gender of the wearer. Females, for example, direct a flow of urine somewhat perpendicularly into a region of the diaper adjacent the wearer's perineum, while a male will direct a flow of urine more toward a region of the diaper adjacent the wearer's pubic area. U.S. Pat. No. 3,559,648 and U.S. Pat. No. 3,766,922 attempted to address this problem by providing diapers with differing concentrations of absorptive material in those areas of the diaper where urine would first impinge and collect. None of these designs, however, have proved entirely satisfactory. Although the urine impingement areas of the gender specific diapers may provide improved region specific absorption, liquid was still able to migrate away from the target regions along the inner liner layer.

It is accordingly a general object of the invention to provide an absorbent garment that inhibits flow of excretions toward the margins of the garment.

Another object is to provide such a garment that enhances absorption of excreta into an absorptive inner layer of the garment.

Another object is to design such a garment that is suited to the unique anatomical requirements of the gender of the wearer.

Yet another object is to inhibit the pooling of liquid waste within the diaper of a recumbent wearer.

Finally, it is an object to provide a diaper that retains human waste within the confines of its borders, away from the skin of the wearer, in a comfortable fashion that is acceptable to the user.

SUMMARY OF THE INVENTION

It has been found that leakage from some disposable absorbent garments may be greater when worn by boys, than by girls, particularly during nighttime wearing. First, during nocturnal use, multiple urine voidings occur and the absorbent material in the garment becomes progressively more saturated after each voiding. Further, a girl may direct a urine stream more directly perpendicular to the inner face of an absorbent garment, whereas the liquid stream from a boy will be directed more tangentially along the inner face of the garment. substantially tangential liquid stream produced by a boy has a velocity and force component directed along the surface that may tend to carry the liquid stream toward a margin of the garment. The flow velocity and force factor result in the liquid stream extending much farther from the source prior to absorption than occurs for a female infant. In either male or female infants, the undesirable free flow of urine is enhanced by a space that is formed between the inner layer of the garment and the skin of the infant when the diaper is deformed from a flat packaging position to a curved use orientation on the body of the wearer.

The present inventors have discovered that the flow of urine across the inner liner of the garment can be reduced by providing barriers or impediments to the urine flow. These impediments are mechanically formed barrier elements, which in an illustrated embodiment are a plurality of deformable loops that project from the inner liner surface of the garment.

In one embodiment, the garment includes a front and rear waistband at longitudinally spaced aspects of the article. The garment includes a moisture impervious outer layer, an absorbent core, an inner liner layer, and an innermost liquid control layer. The liner layer includes a perineal region intermediate the front and rear waistbands, for placement against the wearer's perineum. A plurality of the barrier elements project away from the liner sheet and toward the user's body between the perineum and waistband when the diaper is in place on the user. The barrier elements thereby form a urine stream interference barrier that inhibits the flow of urine toward the waistband.

The liquid control layer of the present invention is particularly useful with male users, because the flow barrier disrupts the tangential or substantially tangential flow of urine across the liner surface toward the front waistband. Wearers of both genders, however, benefit from the barrier because it partially fills the space that is usually present between the skin and inner liner. Occupation of this space by the barrier elements inhibits migration of liquid waste away from the target region where the urine impinges the barrier element. The barrier elements also enhance absorption of the waste into an intermediate absorptive layer of the garment.

In a disclosed embodiment, the barrier elements are deformable loops that project away from the general plane of the liner sheet and toward the user's body when the garment is in place on the user. These loops are capable of lying flat in a compressed condition against the liner layer when the absorbent article is laid or folded flat during packaging. However, the loops assume an elevated position when the absorbent garment is stretched or formed into an operative position with the front and rear waistbands at a waist of the user. The loops or tendrils are preferably disposed in at least one row that extends transversely across the inner liner between the perineal region and a waistband. In other embodiments, multiple rows of loops or other tendrils are positioned diffusely across the inner liner surface. Loops may be of substantially uniform height, or a mixture of short and tall tendrils. They may be randomly distributed across the liner sheet, staggered in patterned or unpatterned groups, and placed in straight rows or tortuous paths.

In a diaper intended for use with a male infant, positioning of the barrier between the perineal region and front waistband is particularly helpful for inhibiting flow of urine across the liner surface and out of the front waistband. Single or multiple rows of barrier elements, such as loops or tendrils, may be placed forward of center in such a diaper. Similar rows would be placed more centrally in a diaper designed to be worn by a female.

In one embodiment, the barrier elements are loops that may be formed by providing slits through the liquid control layer that form elongated strips of the layer between the slits. The strips are substantially flat in adjacent the plane of the liner layer when the absorbent article is flat or folded into a compressed condition (as when packaged in a shipping container). However, the strips are deformed into wide based loops that project away from the liner layer toward the user when the absorbent article is folded into a curved shape to fit about the body of the user. Alternatively, each barrier element may be self-standing, having a front and rear loop portion that are adjoining along a common base adjacent the liner layer.

The barrier elements may be arranged in a variety of configurations on the liner layer. In the embodiment wherein the barrier elements are loops formed from slits and strips in the liquid control layer, the slits may be disposed in transverse rows across the liner layer, with the slits in each row parallel to each other. The slits are not parallel to the longitudinal axis of the garment, hence the loops present at least a partial side face of the loop to the impinging urine stream. The slits preferably are disposed at an angle in a range of 30–60 degrees, and most preferably at about 45 degrees, to the longitudinal axis of the article. A plurality of adjacent rows of slits may be provided, with the parallel slits of one row being on lines which are at an acute angle or substantially perpendicular to the slits of the adjacent row. Hence the resulting elevated loops in the adjacent rows will extend in planes that are perpendicular or at acute angles to each other. This alternating orientation of successive rows of loops helps disrupt tangential flow of urine along the liner surface.

The loop embodiment can be advantageously used not only as a flow barrier to any impinging urine stream, but also as a filler between the liner layer and skin of a user. A sufficient volume of loops can be provided to substantially fill the space between the skin and liner, at least in a target zone where the urine initially impinges against the liner. Alternatively, the loops can substantially fill the crotch area between the liner and skin of the perineum, pubic area and lower buttocks. These loops help fill the potential space between the liner and skin, and inhibit migration of excretions to lower lying areas of the diaper in a recumbent user. The loops promote absorption into the core by stopping the flow of urine along the liner surface of the diaper, and providing an underlying opening into the liner layer that provides a channel into the absorbent core.

In another embodiment, the loops are preformed on the inner liner surface, and do not require barrier activation by stretching the diaper or folding it into a curved shape. The loop is a freestanding strip of material (for example, liquid control layer material) that is secured to itself along an edge that is contiguous with the liner surface. The loops are small and pliable, such that they are substantially flat against the liquid control layer when the diaper is packed in a box with other diapers in a flat condition. However, the loops are sufficiently resilient that they rise at least slightly away from the plane of the liner layer when the diaper is not compressed by the weight of surrounding diapers, and form tendrils that reach out away from the diaper surface to interfere with liquid flow.

The term "tendril" as used herein refers to an elongated projection, preferably extending a distance away from the diaper surface greater than its width, and which is capable of curling, forming a loop, and/or interfering with the flow of liquid directed tangentially or substantially tangentially across the inner surface of a diaper or other absorbent garment. A "substantially tangential" flow is a flow directed at an angle of 0–45 degrees to the inner surface of the diaper.

BRIEF DESCRIPTION OF THE DRAWINGS

FIG. 9 is a top plan view of the inner surface of a third embodiment of the invention, having a single row of interdigitating tendrils.

FIG. 10 is an enlarged view of the row of interdigitating tendrils of FIG. 9 before activation of the tendrils to an elevated operative position.

FIG. 11 is a view similar to FIG. 10, but with the tendrils raised to an activated position.

DETAILED DESCRIPTION OF PREFERRED EMBODIMENTS

Figure 2:
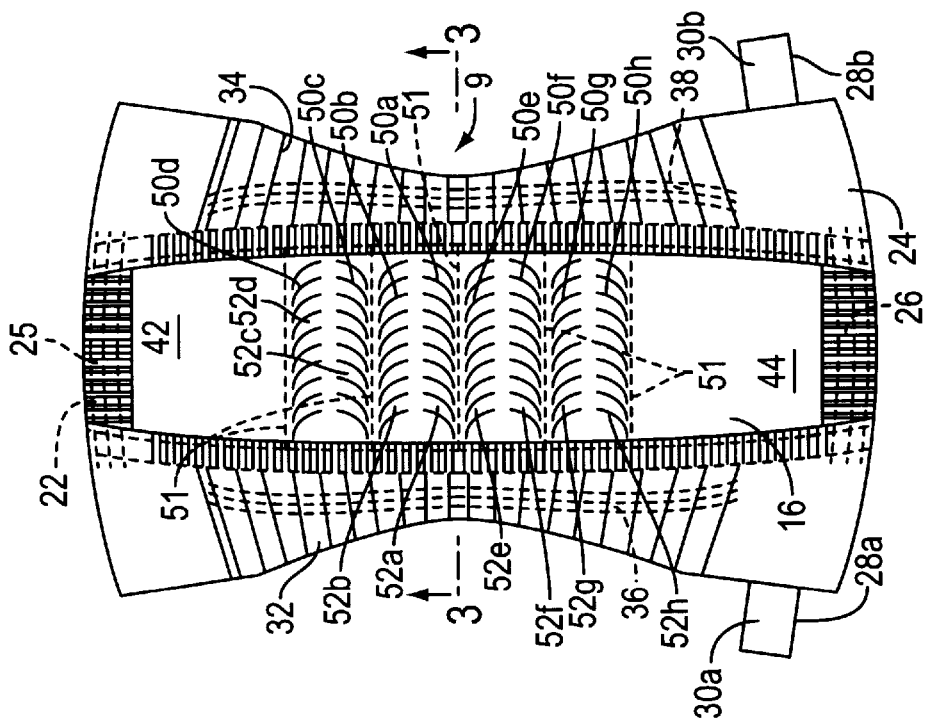
FIG. 2 is a view of the diaper of FIG. 1 contracted along its longitudinal and transverse axes by the elastic gathers.

An absorbent article made in accordance with selected embodiments of the present invention is shown in FIGS. 1–4. A particular embodiment of the invention is diaper 9, or an adult incontinence brief having a moisture-impervious backing layer 10 (FIG. 3), inner liner sheet 12, and a moisture-absorbent layer, core or pad 14 between layers 10 and 12. A liquid control layer 16 is apposed to the inner surface of liner sheet 12. The manufacture of disposable absorbent garments, baby diapers and adult incontinence briefs is generally known in the art. For instance, absorbent articles and methods for their manufacture are illustrated in U.S. Pat. Nos. 4,726,807 and 4,687,477, both of which are incorporated by reference.

Figure 3:
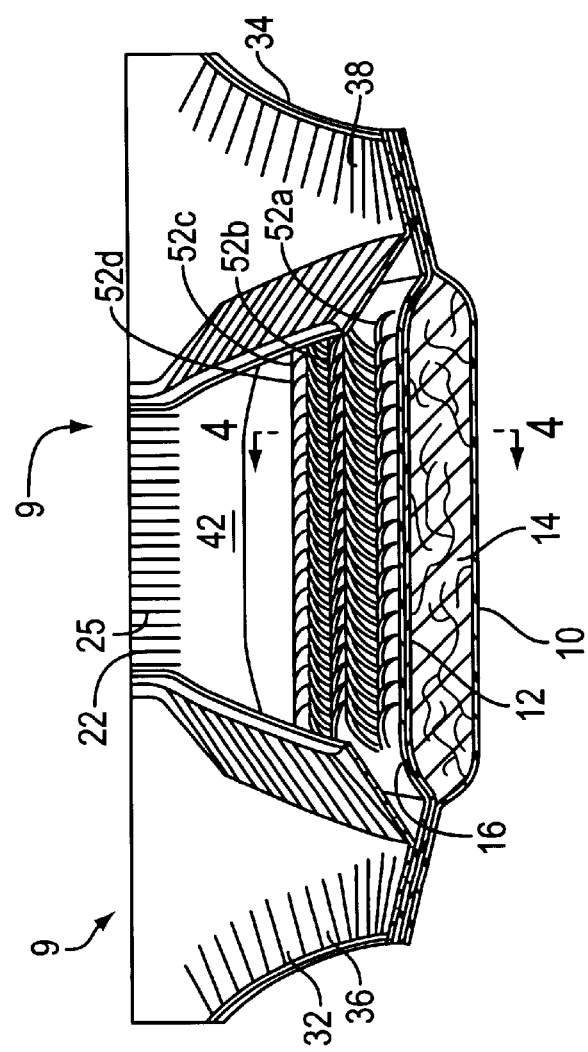
FIG. 3 is an enlarged view, partially in cross-section, taken along line 3—3 of FIG. 2.

In the illustrated embodiment, absorbent pad 14 is disposed between the backing layer 10 and the liner sheet 12, as shown by FIG. 3. One skilled in the art will appreciate that additional layers, such as additional impervious layers, also can be added. The liner sheet 12 and backing layer 10 may be bonded together, at least in the leg opening portion of the article, by any known means. One example of a method for bonding the layers 10 and 12 together is to place an adhesive in discrete locations. Alternatively, layers 10 and 12 can be sonically bonded together.

Liner sheet 12 inhibits pulp fibers in the absorbent pad 14 from migrating inwardly, and escaping through apertures in the liquid control layer 16 that are described below. A liner sheet need not be used, for example, if containment of the diaper's interior is not desired. The liner sheets would be optional, for instance, if the diaper has a compressed composite absorbent core or a super absorbent sheet, such as a foam or web based super absorbent polymer (SAP). Even if containment of interior components is not desired, the liner sheet 12 is also useful as a transfer layer that distributes urine into unused portions of absorbent pad 14, and diminishes the reflux of liquid back through liquid control layer 16 when the shifting weight of the wearer compresses pad 14 and expresses liquid from it.

Absorbent pad 14 is typically made of wood pulp or other absorbent fibers, such as a commercially available fluff pulp or a fluffed soft-wood pulp. Core or pad 14 may have a substantially hourglass shape. Alternatively, the pad 14 also may have a substantially rectangular shape. The absorbent core or pad 14 is generally located in at least a perineal region 46 of the article, but may extend more extensively throughout the diaper toward the waist bands. Superabsorbent particulate matter can be used in combination with the wood pulp or absorbent fibers to produce a core 14 permeated with superabsorbent particles, thereby enhancing its absorptive properties.

Figure 1:
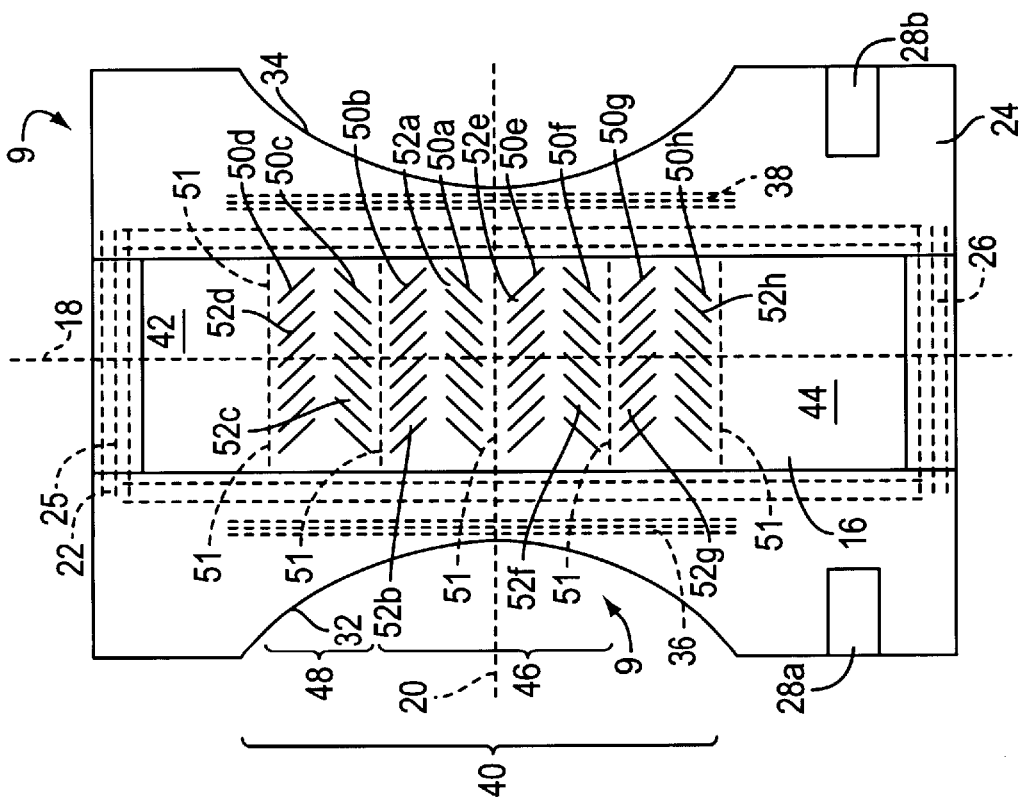
FIG. 1 is a top plan view of the inner surface of a disposable diaper made in accordance with an embodiment the present invention, the diaper being stretched flat against the action of its elastic gathers.
Figure 5:
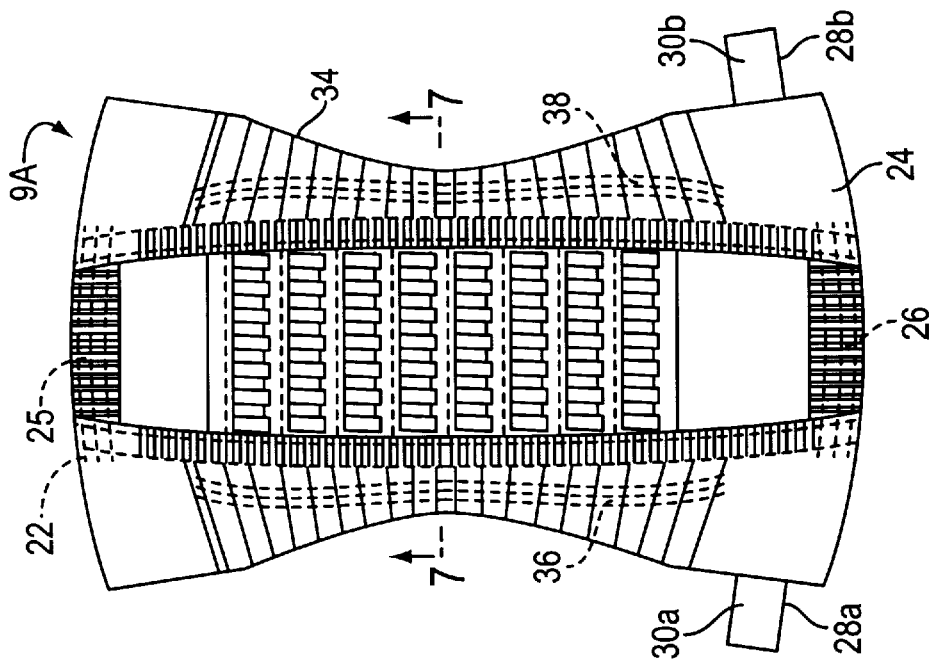
FIG. 5 is a top plan view of a second embodiment of a diaper of the present invention, stretched out flat, in which the loops are preformed freestanding tendrils.
Figure 6:
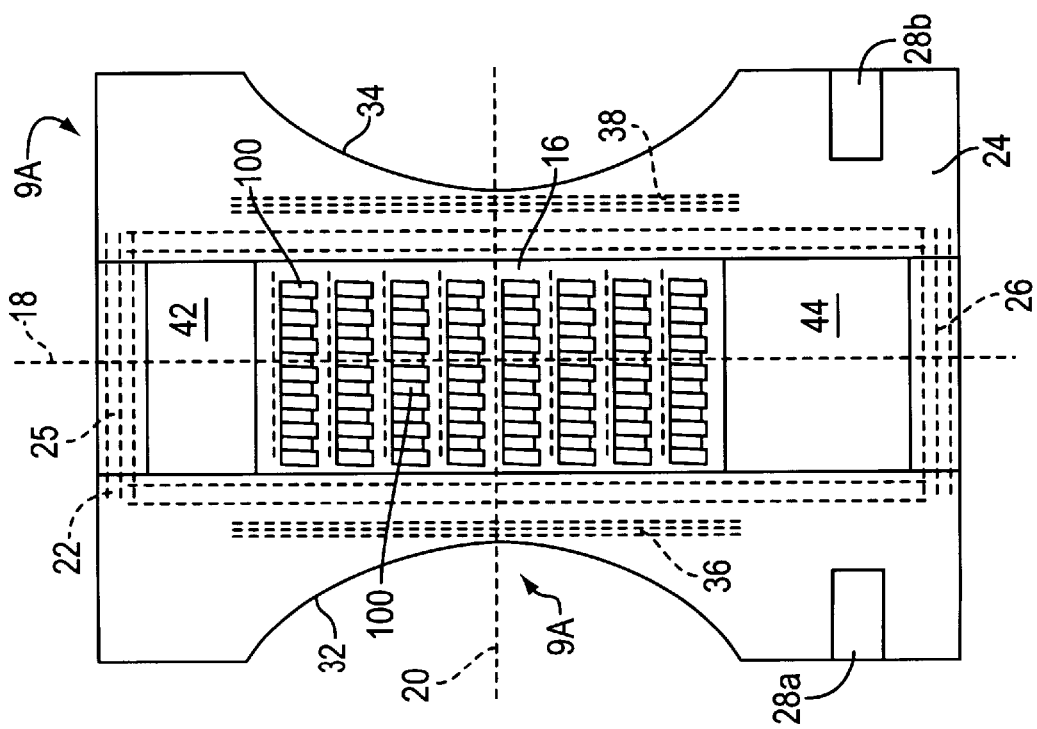
FIG. 6 is a view of the diaper of FIG. 5 contracted along its longitudinal axis by the elastic gathers.

FIGS. 1, 5 and 9 illustrate three different embodiments designated diapers 9, 9A and 9B. Like parts of the three embodiments are designated by the same reference numbers. The diapers 9 and 9A are each shown having a longitudinal axis 18 and a transverse axis 20. A front waistband 22 extends along one transverse border of the diaper, while a rear waistband 24 extends along the other transverse border thereof. Waistbands 22, 24 occupy longitudinally spaced margins that are each about one inch wide (as measured in the longitudinal direction). The front and rear waistbands contain elastic gathers 25, 26 that exert traction in a transverse direction to gather the waistbands 22, 24 around the waist of a wearer, and help it conform in a more liquid-tight configuration to the anatomical of the waist. The elastic gathers in the diaper may be made from natural rubber, polyurethane, lycra strands, and other elastic materials known in the art.

Tapes or other fastener tabs are located at transversely opposing edges of the rear waistband 24. The tabs are contiguous with and extend in the same plane as the waistband 24, for securing diaper 9 about the waist of a person wearing the diaper. FIGS. 1 and 2 show a pair of tape fastener tabs 28a, 28b in one illustrated embodiment of fasteners useful for securing the diaper in place. FIG. 1 shows the tabs 28a, 28b folded over to lie flush with the inner liner surface 12 during storage and shipment, while FIG. 2 shows the fastener tabs in a fastening position extending generally transversely away from rear waistband 24. An inner face 30a, 30b of the respective tabs is coated with an adhesive material, which can be protected during storage by a plastic cover sheet (not shown) that is pulled away from the adhesive face prior to fixing the garment in place on a user.

The moisture impervious backing layer 10 may be made from a thin thermoplastic material such as a polymer film. For example, layer 10 can be composed of a thin polyolefin film, such as polypropylene or polyethylene. In yet other embodiments, backing layer 10 can be composed of a liquid-impermeable microporous polyethylene film, or a nonwoven spunbonded layer that has been completely or partially coated with a polymer film to provide a sufficient level of liquid impermeability in selected regions of the backsheet.

Liner sheet 12 is typically an integral sheet of a moisture pervious material, and may comprise a composite material having different degrees of moisture permeability. Examples of suitable liner layer materials are liquid permeable, substantially hydrophobic fibrous material, such as a spun-bonded web composed of synthetic polymer fibers. Alternatively, liner layer 12 may be a melt-blown web or a bonded-web of synthetic polymer fibers. Suitable synthetic polymers include polyethylene, polypropylene and polyesters. A particularly suitable material for liner sheet 12 is a spun-bond polypropylene material having a basis weight of about 0.6 ounces per square yard. However, one skilled in the art of absorbent garment manufacture will realize that a wide variety of materials may be used to form backing layer 10, liner sheet 12, and absorbent core 14. This invention is intended to encompass all such materials, and is not limited to the specific materials that are discussed herein.

FIGS. 1 and 5 illustrate substantially hourglass-shaped diapers each having a first in-cut, arcuately recessed leg opening 32 and a second in-cut, arcuately recessed leg opening 34. Leg openings 32, 34 are semi-ellipses elongated in the direction of longitudinal axis 18, and are bisected into elliptic quadrants by the transverse axis 20 of the diapers. The intersection of axes 18, 20 is designated the center of the diaper. An elongated elastic gather strip 36, 38 extends adjacent the margin of each opening 32, 34 to gather the leg openings around the thigh of an infant or other person wearing the diaper.

A crotch region 40 (FIG. 1) of diaper 9 is the area of the diaper between leg openings 32, 34. The inner surface area of the diaper may further be subdivided into several subsections. The area of the diaper between the crotch region 40 and front waistband 22 is a front panel 42, while the area between the crotch region 40 and rear waistband 24 is a rear panel 44. The crotch region is further divided into a perineal region 46 configured to fit against a perineum of a user when the diaper is in place on a user, and a male target region 48. The target region corresponds roughly to the area of the liner that fits against the pubic region of the wearer, and is the region of the diaper where urine from a male user often first impinges against liner 12. series of rows of slits 50 is provided through the crotch area of liquid control layer 16 to form barrier elements such as loop or hump impediments to the flow of urine within the diaper when urine impinges against the liner layer. The illustrated rows of slits are designated "a–h" in FIGS. 1 and 2. For example, all the slits in row a are designated 50a. Each row extends at an angle to the longitudinal axis 18, and in the illustrated embodiment the rows extend perpendicular to longitudinal axis 18. The slits within each row (for example slits 50a within row a) are parallel to each other, but the parallel slits within each row are disposed at an acute angle to the longitudinal axis 18. This acute angle is preferably 30–60 degrees to the axis 18, but is illustrated in FIGS. 1 and 2 at a particularly preferred angle of 45 degrees. In the embodiment illustrated in FIGS. 1 and 2, liquid control layer 16 is adhered to underlying liner 12, for example, by linear distributions of glue 51 (shown as broken lines in the drawings) extending transversely across the diaper between layers 12 and 16. In the disclosed embodiment, the glue line 51 is placed between every other row of slits 50 (between rows 50b, c,; 50a, e, and rows 50f, g) to secure layer 16 to layer 12.

Figure 4A:
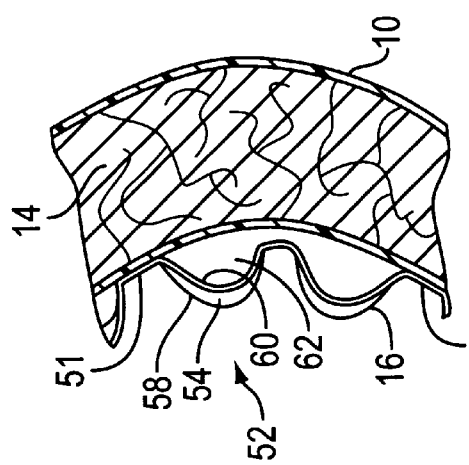
FIG. 4A is an enlarged fragmentary cross-sectional view of the diaper of FIG. 1, folded into an arcuate operative position for placement about a user, showing the loops in an activated raised position away from the inner liner of the diaper.
Figure 4B:
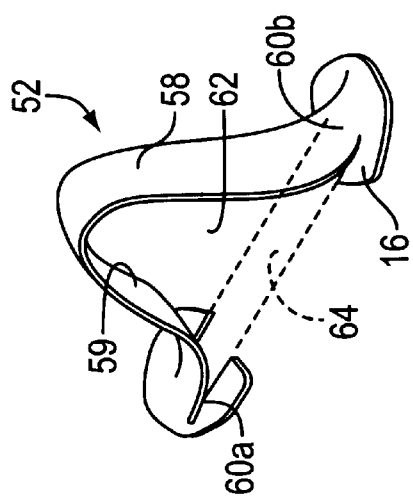
FIG. 4B is an enlarged schematic view of a single loop on the inner liner.

The slits 50 of each row form a plurality of aligned strips 52 between the slits. Strips 52 are designated 52 a–h to specify among the rows of strips shown. For example, all the strips in row a are designated 52a. The strips 52 are flat against layer 12 and contained within the plane of layer 16 when the diaper 9 is in a flat orientation, as shown in FIG. 1, with backing layer 10 and inner liner sheet 12 substantially flat and parallel to each other. This is a position the strips would have when the diaper is stacked flat in a container with other diapers, or tri-folded for packaging. However, the central regions of the strips move up and out of the plane of layer 16 when the surface area of the diaper is stretched prior to use, and/or subsequently contracted by the elastic to the shape shown in FIGS. 2 and 3. Movement of the strips out of the plane of the liquid control layer is further promoted by bending of the diaper into an arcuate or curved configuration for placement about the body of a user, as shown in FIG. 4.

As the diaper is curved into an arc for placement about a user, the radius of curvature of the liner layer 12 is greatly reduced. Moreover, the elastic gather strips 36, 38 create corrugations in the liner layer 12 that also compress the surface area of the liner layer, particularly shortening the longitudinal dimension of layer 12. These actions also help force strips 52 away from liner layer 12, to form a row of standing loops or narrow humps (as best illustrated in FIGS. 4, 4A) that form barriers to urine flow. The attachment of liner 12 to layer 16 along glue lines 51 helps transfer the distortion and stretching forces from liner layer 12 to layer 16 for activation of the loops.

The strips 52 are apposed against and parallel to the plane of liner 12 when the diaper is in the flat orientation of FIG. 1. When the diaper is folded into an arc, as shown in FIG. 4, the distance between regions 60a, 60b on a portion of a strip 52 (as seen in FIG. 4A) decreases, which causes the strip 52 to rise away from the plane of liner 12 into a loop 60, as shown in FIG. 4A. As the strips 52 elevate out of the liner plane, rows of loops are formed, corresponding to the rows of strips a–h from which the loops are formed. As best shown in FIGS. 4 and 4A, each loop forms a hump or protuberance with a convex upper surface 58, and a concave inner face 59 that defines an aperture 62 between strip 52 and a slot or aperture 64 in the surface of layer 16 from which strip 52 is raised. The aperture 62 advantageously provides an ingress for entry of liquid into underlying liner 12. Hence, the apertures act as "sewers" that help absorb liquid waste captured by the barrier elements.

The slits 50 may be arranged in tandem rows that cooperatively present barriers to the flow of urine the inner surface of the diaper. Tandem rows are side by side rows, such as rows 50 a and e; rows 50 b and c; or rows 50 f and g. Each of slits 50 is inclined at an acute angle to longitudinal axis 18 of diaper 9, such that the standing loop formed by the strip 52 will extend outwardly from liner 12 in a plane that is not parallel or perpendicular to the axis 18. This arrangement has the advantage of presenting a greater surface area of the loop face to an oncoming stream of urine that substantially tangentially impinges inner layer 12 in the general direction of axis 18.

In a preferred and illustrated embodiment as shown in FIG. 1, the slits of tandem or adjacent rows are at an acute angle to axis 18; they are neither parallel nor perpendicular to axis 18. For example, parallel slits 50a are arranged at an angle to axis 18 (for example on a line intersecting axis 18 at an angle of about 45 degrees). Parallel slits 50e are also disposed at an angle to axis 18 (for example on a line intersecting axis 18 at an angle of about 45 degrees). Moreover, although corresponding tandem slits 50a and 50e are not connected, they are on lines that also intersect each other at an angle, being for example at approximately 90 degree angles to one another. With the slits in this relative orientation, the strips 52a are approximately perpendicular to the strips 52e when the diaper is folded into an arcuate shape for use.

Similarly tandem rows of slits 50b, 50c and tandem rows of slits 50f, 50g are disposed at a right angle to one another, such that the loops formed by these tandem rows are also approximately perpendicular to one another. Hence each tandem row of loops formed from strips 52a and e, 52b and c, and 52f and g, will form a series of intersecting loops that almost meet at a common intersection adhered to the liner surface by a linear distribution of glue 51. As best shown in FIG. 3, alternating orientations of the loops present different surface configurations to an oncoming stream of urine, and help break up an impinging stream of urine reducing the flow and velocity of the impinging stream.

Although a 90 degree angle between the loops of tandem rows is shown in the preferred embodiment, a variety of angles may be used, for example 45 to 135 degrees, more preferably 80 to 100 degrees, but most preferably an angle of about 90 degrees. The perpendicular relationship of the strips in adjacent rows maximizes the flow disrupting properties of the protuberances. Any gap between adjoining loops in a given row is effectively blocked by a loop in the tandem row. Hence, the loops are staggered, with a loop in a first row filling a gap between adjacent loops in a second row.

Rows d and h are not shown in a tandem pair, to illustrate that the invention also includes embodiments in which rows are not paired. The loops may be arranged in the perineal region and on the inner faces of the front and rear panels to partially occupy or substantially fill a space or potential space between the skin of a user and the inner liner layer. In some embodiments, the loops are located only in the perineal region 46 or crotch region 40. In yet other embodiments, the loops may be located only on the front panel, or rear panel, or both. In particularly preferred embodiments, the loops are located at least in a target region of the inner liner, which is on the inner face of the front panel between the perineal region and front waistband.

After manufacture, the diaper is stored in a flat position, such as shown in FIG. 1, or folded (not shown), with the loops flat in the plane of layer 16. When the diaper is removed from a storage container and stretched, the strips 52 are activated to rise to form loops, as shown in FIG. 4A. The diaper is then placed on the user, with the front and rear waistbands at the front and rear waist of the user. Backing material is removed from tabs 28a and 28b, and the diaper is secured to the user by adhering the adhesive tabs from the rear to an adjoining portion of the front waistbands, such that the diaper is snug around the waist. The user's legs will protrude through the leg holes formed by leg openings 32, 34. Elastic gathers help conform the waistbands and leg openings to the skin of the user, and inhibit leakage of waste material from the diaper during use.

Another embodiment of the diaper is shown in FIGS. 5–8, wherein like parts have been given the same reference numbers as in the embodiment of FIGS. 1–4. This embodiment does not have rows of strips that are activated during use to form barriers. The barrier members of this embodiment are instead preformed tendrils, for example, formed by redundant folds of liner layer that are cut into a series of side by side loops. As seen in FIG. 5, the loops 100 are arranged in a plurality of rows across a portion of the width of liner surface 12. In other embodiments (not shown), the loops may be arranged randomly across the surface of liner 12.

Figure 8:
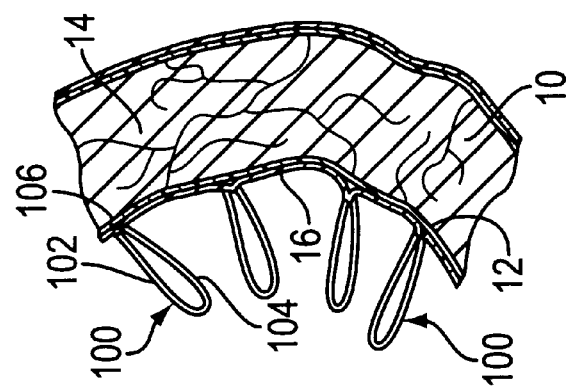
FIG. 8 is an enlarged cross-sectional fragmentary view of the diaper of FIG. 5, taken along line 8—8 of FIG. 7, with the diaper folded into an arcuate operative position.
Figure 7:
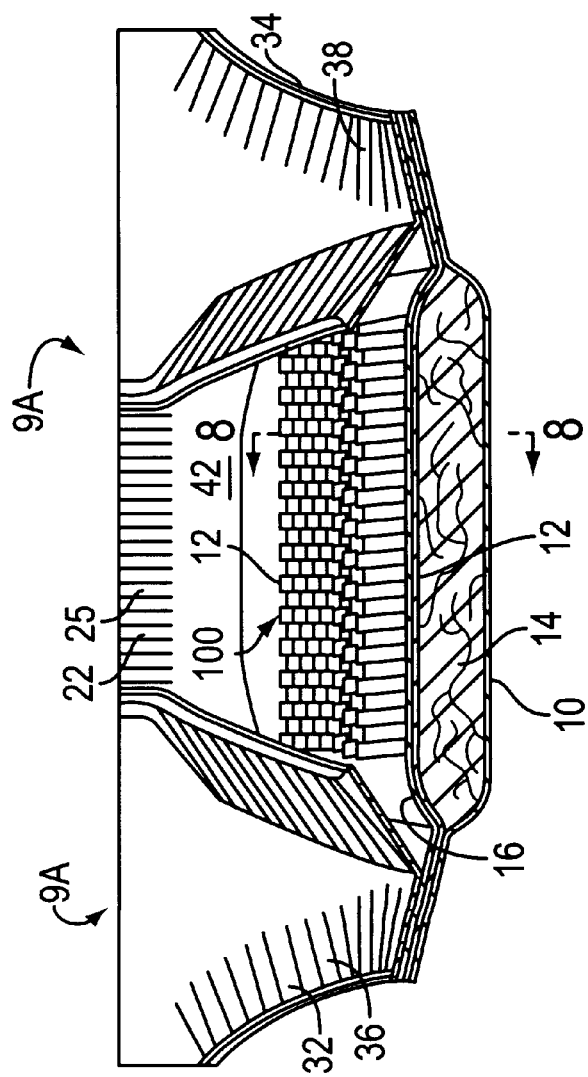
FIG. 7 is an enlarged view, partially in cross-section, taken along line 7—7 of FIG. 6.

As shown best in FIG. 8, each tendril loop 100 is a self-standing protuberance that has a front loop portion 102 and a rear loop portion 104. The front and rear portions 102, 104 are adhesively joined to one another along a common edge 106.

In the illustrated embodiments of FIGS. 1–8, the loops are arranged in parallel rows. The width of the loops is at least 2 mm, preferably 2 to 5 mm. The spacing between the loops in a single row is preferably no greater than the loop width, although the disclosed embodiments show them side by side. The rows of loops are preferably spaced such that 90% of all angles that urine could travel will contact a loop within 5 cm of linear travel on the liquid control layer. The inventors have found that this goal may be achieved by spacing the rows of loops no more than 3 cm apart. Loop density preferably varies from 6 loops per square inch for a 2 mm wide loop, to 3 loops per square inch with a 5 mm wide loop. Adjacent loops in each row may be short and long, for example 1 mm long and 20 mm long. Alternatively, the loops may be disposed randomly in the target area of the diaper, or throughout the entire crotch area of the diaper. The loops provide an impediment to substantially tangential flow of urine along the liner surface, and also fill the potential space between the skin of the user and the liner surface. Interruption of this flow disrupts the movement of urine, and other liquid or semi-liquid wastes, toward the more peripheral regions of the diaper from which the waste can escape the confines of the diaper. Filling of the space between the user and liner also inhibits liquid movement within the diaper.

The void space the tendrils or other loops are designed to fill is up to 2 cm distance between the inner surface of the layer and the baby's skin. In preferred embodiments, at least 80% of the tendrils or other loops contact the baby's skin (i.e., at least 80% of the barrier elements project 2 cm away from the inner liner layer of the diaper) after the elements have been activated. A preferred average barrier element height distribution of the activated loop is 1.6 cm from the diaper surface to the peak of the loop with a range of height from 0.1 cm to 2.0 cm.

Yet another embodiment of the garment is shown in FIGS. 9–11, wherein diaper 9B is similar in overall construction to diapers 9 and 9A earlier described, with like parts designated with like reference numbers. Diaper 9B differs, however, in that it has only a single pair of tendril rows 120a, 120b extending along the transverse axis of the diaper. The tendrils are formed from a series of interdigitating strips 122a, 122b that are elevated to the activated orientation shown in FIG. 11 by stretching the diaper. The strips 122a, 122b are cut in an elongated rectangular piece of material 124 that is glued to inner liner 12.

Figure 12:
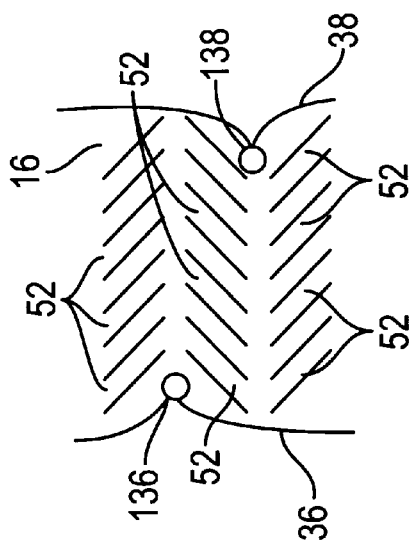
FIG. 12 is a schematic view of another embodiment of the invention having a single row of tendrils standing side-by-side.

The embodiment of FIG. 12 shows a single row of tendrils 130 of uniform height that are formed from an elongated transversely extending fold of a liquid layer 132 folded against itself and glued along a base portion 133 to inner liner 12. The transverse fold of material is cut into a plurality of adjacent strips 134 by placing parallel cuts of equal length in the upstanding fold of material. In the disclosed embodiment, the cuts are equally spaced such that the strips are of uniform width and side-by-side.

Figure 13:
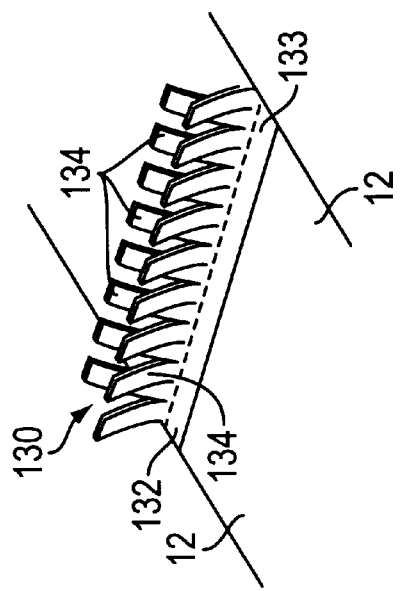
FIG. 13 is a schematic view of the liquid control layer of yet another embodiment of the invention, with slits through the liquid control layer to form loops, and adhesive welds of the liquid control layer to elastic leg gathers.
Figure 14:
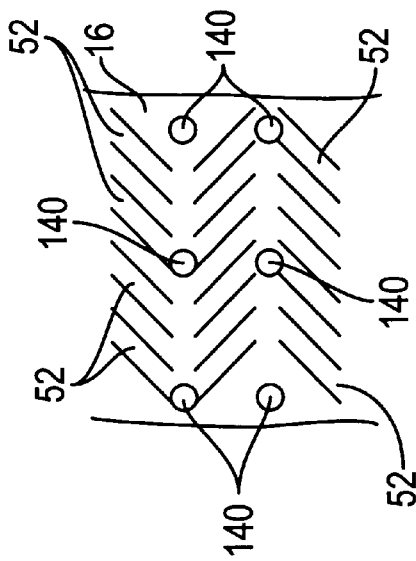
FIG. 14 is a schematic view similar to FIG. 13, but showing a different arrangement of the adhesive welds to subjacent layers.

Additional embodiments of the invention shown in FIGS. 13 and 14 illustrate alternative attachments of liquid control layer 16 to underlying liner 12. As in earlier embodiments, layer 16 is provided with rows of parallel strips alternately inclined in different directions. These slits form rows of strips 52. Spots of adhesive 136, 138 attach the edges of liquid control layer 16 to leg gathers 36, 38. Alternatively, as shown in FIG. 14, a series of spots of glue 140 is distributed between rows of strips 52 to adhere layer 16 to an underlying layer 12 (not shown in FIG. 14). These adhesive spots transfer stretching actions of liner 12 to overlying layer 16 to activate the flat strips 52 into loops such as those shown in FIG. 4A. Although the glue spots 140 are shown placed in regular rows in FIG. 14, the spots may be randomly distributed.

Figure 15:
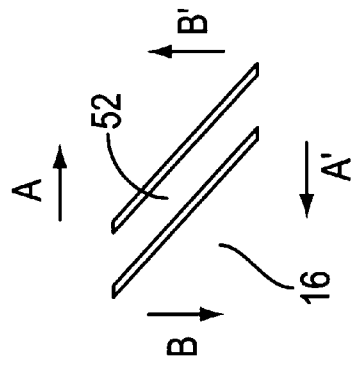
FIG. 15 is a schematic view illustrating some of the forces that help activate the loops.

Some of the vector forces that are exerted on liner 16 through adhesive spots 136 or 140 are illustrated in FIG. 15. Transverse vectors A, A' and longitudinal vectors B, B' displace the ends of strip 52 towards each other to help raise a central portion of strip 52 out of the plane of layer 16.

Having illustrated and described the principles of the invention in preferred embodiments, it should be apparent to those skilled in the art that the invention can be modified in arrangement and detail without departing from such principles. Therefore, the illustrated embodiments should be considered only as preferred examples of the invention and not as a limitation on the scope of the claims. I therefore claim as my invention all modifications and equivalents the illustrated embodiments coming within the scope and spirit of the following claims.

We claim:

1. An absorbent garment, comprising:
   a backsheet layer;
   a substantially liquid-permeable inner liner layer, an absorbent layer between the backsheet and inner liner layers;
   a front waistband and a rear waistband at spaced end regions of the article;
   a crotch region between the front and rear waistbands; and
   a liquid control layer over the inner liner layer, said liquid control layer having a plurality of barrier elements projecting away from the inner layer and toward a user's body when the article is in place on the user, to form a flow interference barrier to urine, wherein the barrier elements are elongated projections formed by slits through the liquid control layer such that portions of the barrier elements project from a remainder portion of the liquid control layer, and away from the garment;

wherein the barrier elements extending away from the garment are present in a density of 3–6 barrier elements per square inch of liquid control layer surface area, and the barrier elements have a length in the range of 1–20 mm.

2. The absorbent garment of claim 1 wherein the plurality of barrier elements are deformable loops that establish the barrier elements as partially discontinuous with the liquid control layer, wherein the deformable loops are configured to be in a compressed condition when the absorbent article is in a stored condition, and substantially all the loops assume an elevated position projecting away from the garment when the article is in an operative position with the front and rear waistbands at a waist of the user, with a row of the deformable loops arranged transversely in a front target region of impingement of urine against the inner liner layer.

3. The absorbent garment of claim 2 wherein the barrier elements are arranged in a plurality of substantially parallel rows, wherein the rows are longitudinally spaced such that they do not overlap, but are no more than 3 cm apart, a distance between the slits that form each barrier element is 2–5 mm, a distance between adjacent barrier elements is no greater than a width of an adjacent barrier element, and a loop density of loops projecting away from the garment is 3–6 loops per square inch.

4. The absorbent garment of claim 1, wherein the barrier elements projecting away from the garment are provided in sufficient density to substantially fill a space between the user's body and a front target area of the inner liner layer, where urine initially impinges from a user, when said garment is worn by the user.

5. The absorbent garment of claim 1 wherein said plurality of barrier elements comprises three or more barrier elements.

6. The absorbent garment of claim 1 wherein the inner liner layer further includes a perineal region intermediate the front and rear waistbands, for placement against the user's perineum, the garment further comprising a plurality of rows of barrier elements projecting away from the garment in a male urine target region between the perineal region of the inner liner layer and the front waistband.

7. The absorbent garment of claim 6 wherein the barrier elements being loops formed by the slits in the liquid control layer.

8. The absorbent garment of claim 7 wherein the barrier elements are spaced such that 90% of all angles that urine could travel will contact a loop projecting away from the garment within 5 cm of linear travel.

9. The absorbent garment of claim 7 wherein the loops are defined by slits in the liquid control layer, and the slits form elongated strips between the slits, wherein the strips lie substantially flat against the inner liner layer prior to an activation step, and central regions of the strips project out of the liquid control layer, away from the inner liner layer, toward the user when the garment is worn by the user.

10. The absorbent garment of claim 9 wherein the barrier elements are defined by slits that cooperatively define loops, the width of each strip is at least 2 mm, the length of each strip is at least 10 mm, and the loops extend away from the remainder portion of the liquid control layer when the article is in an arc as it would be disposed around the body of the user, with the loops projecting toward the user.

11. The absorbent garment of claim 9 further comprising a plurality of connections between the liquid control layer and inner liner layer to transfer stretching forces in two substantially perpendicular directions from the inner liner layer to the liquid control layer, to move transversely displaced ends of the strips towards each other to raise a central portion of each strip away from the garment.

12. The absorbent garment of claim 9 wherein the liquid control layer is elongated and the strips are disposed in a transverse row across said liquid control layer, and the strips are disposed at an acute angle relative to a longitudinal axis of the absorbent garment such that the loops present partial side faces to a longitudinal flow of urine along the liquid control layer, wherein the partial side faces form a flow interference barrier to an impinging stream of urine directed substantially tangentially of the inner liner layer.

13. The absorbent garment of claim 12 wherein the strips are arranged in a plurality of adjacent rows of strips, the strips of a first row of strips are disposed at an acute angle to the strips of an adjacent row, and the first row of strips does not overlap in the longitudinal direction with the strips of the adjacent row.

14. The absorbent garment of claim 12 wherein the strips are disposed in a plurality of nonoverlapping rows, adjacent loops in a row are no farther apart than a width of the loops, and the strips in each transverse row of slits are disposed at an angle of about 30 to 60 degrees to the longitudinal axis of the article.

15. The absorbent garment of claim 14 wherein strips within each transverse row are parallel to strips within the same row, but substantially perpendicular to strips within an immediately adjacent row.

16. The absorbent garment of claim 15, wherein the strips are arranged in adjacent parallel rows with the strips in a first row disposed substantially perpendicular to the strips in an immediately adjacent row such that each pair or adjacent rows presents side faces of the loops that lie in alternating, staggered perpendicular planes projecting away from the garment, with gaps between adjoining loops in a row being blocked in the longitudinal direction by a loop in the adjacent row, to interfere with longitudinal flow of urine along the liquid control layer.

17. An elongated absorbent article, comprising:

a backsheet layer;

a substantially liquid-permeable inner liner layer;

an absorbent layer between the backsheet and inner liner layers;

a liquid control layer on an inner surface of the inner liner layer;

a front waistband and a rear waistband at longitudinally spaced regions of the article;

a perineal region of the absorbent article configured to fit against a perineum of a user;

a target region of the liquid control layer, against which urine from a user first impinges substantially tangentially when the article is worn by the user; and a series of rows of slits through the liquid control layer, each row extending substantially perpendicular to a longitudinal axis of the article, the slits in each row being disposed at an acute angle to the longitudinal axis of the article, the slits in each row forming a plurality of aligned strips in the liquid control layer, wherein the strips form a row of loops projecting away from the absorbent layer, and the loops are configured to be in a first compressed condition against the liner layer, and to assume an elevated position with substantially all the loops at least partially projecting toward the user when the article is in an operative position on the user.

18. The absorbent article of claim 17 wherein the rows of loops are disposed in the target region, which is between the perineal region of the absorbent article and the front waistband thereof.

19. The absorbent article of claim 17 wherein the rows comprise adjacent pairs of first and second rows, and the slits of the first row intersect the longitudinal axis of the article at an acute angle to the slits of the second row.

20. The absorbent article of claim 17 wherein the rows of loops are disposed between the perineal region of the absorbent article and the front and rear waistbands.

21. The absorbent article of claim 17 further comprising a plurality of connections between the inner liner layer and liquid control layer to transfer stretching forces in at least two directions from the inner liner layer to the liquid control layer, and raise the strips into loops that project away from the article.

22. The absorbent article of claim 21, wherein the plurality of connections comprise connections that transfer stretching forces in two substantially perpendicular directions from the inner liner layer to the liquid control layer.

23. The absorbent article of claim 22, wherein one of the perpendicular directions is parallel to a longitudinal axis of the garment.

24. An elongated absorbent garment, comprising:
a backsheet layer;
a substantially liquid-permeable inner liner layer;
an absorbent layer between the backsheet and inner liner layers;
a liquid control layer on an inner surface of the inner layer;
a front waistband and rear waistband at longitudinally spaced regions of a plurality of slits through the liquid control layer, wherein the slits form loops that project away from the absorbent layer when the absorbent garment is worn by a user, to form a barrier in a pubic target region of the garment between a perineal region and the front waistband;
wherein the loops have a length in the range of 1–20 mm and are present in a density of from 3–6 loops per square inch of liquid control layer surface area.

25. The absorbent garment of claim 24, wherein the loops, that project away from the absorbent layer when the absorbent garment is worn by the user, are spaced no farther apart than a width of the loops, and substantially fill a space between the liquid control layer and the user.

26. The absorbent garment of claim 24, wherein at least about 80% of the loops formed by the plurality of slits contact the user when the garment is worn by the user.

27. An elongated absorbent garment, comprising:
a backsheet layer;
a substantially liquid-permeable inner liner layer;
an absorbent layer between the backsheet and inner liner layers;
a liquid control layer on an inner surface of the inner liner layer;
a front waistband and a rear waistband at longitudinally spaced regions of the article;
a perineal region of the absorbent garment configured to fit against a perineum of a user;
a front target region of the liquid control layer, against which urine from a male user first impinges substantially tangentially when the article is worn by the user;
a series of rows of slits through the liquid control layer, wherein the rows do not overlap in a longitudinal direction, and each row extends substantially perpendicular to a longitudinal axis of the garment, the slits within each row being substantially parallel to each other and disposed at an acute angle to a longitudinal axis of the garment, the slits in each row forming a plurality of aligned strips in the liquid control layer, wherein each row of slits and strips forms a row of side-by-side loops projecting away from the absorbent layer, and the loops are configured to be in a first compressed condition within the liquid control layer when the garment is stored in a stretched condition, and the loops assume an elevated position with substantially all the loops projecting away from the garment and toward the user when the garment is in an operative position on the user, wherein at least one of the rows of loops is located in the front target region of the garment;
wherein the strips in a row are substantially perpendicular to strips in an immediately adjacent row, such that each pair of adjacent rows presents side faces of the loops that lie in alternating perpendicular planes to interfere with longitudinal flow of urine along the liquid control layer;
a plurality of connections between the inner liner layer and liquid control layers that transfers first and second stretching forces from the inner liner layer to the liquid control layer to move the loops to the elevated position, wherein the first stretching force is directed substantially parallel to the longitudinal axis of the garment, and the second stretching force is directed substantially perpendicular to the longitudinal axis of the garment; and
wherein the loops are present in a density of 3–6 loops per square inch of liquid control layer surface area, a width of each strip is at least 2 mm, adjacent loops in a row are spaced no greater than the width of each strip, a length of each strip is at least 10 mm, and the loops are placed such that 90% of all angles that urine could travel will contact a loop projecting away from the garment within 5 cm of linear travel on the liquid control layer.

* * * * *